(12) United States Patent
Del Bon et al.

(10) Patent No.: US 6,270,223 B1
(45) Date of Patent: Aug. 7, 2001

(54) ACTIVE ELECTRO-OPTICAL FILTER DEVICE AND GLARE-PROTECTION DEVICE

(75) Inventors: Franco Del Bon, Aarburg (CH); Phillip Syré, Linden (DE); Leo Keller, Bertschikon (CH)

(73) Assignee: Optrel AG, Watwil (CH)

( * ) Notice: Subject to any disclaimer, the term of this patent is extended or adjusted under 35 U.S.C. 154(b) by 0 days.

(21) Appl. No.: 09/446,091

(22) PCT Filed: Jun. 12, 1998

(86) PCT No.: PCT/CH98/00258

§ 371 Date: Dec. 17, 1999

§ 102(e) Date: Dec. 17, 1999

(87) PCT Pub. No.: WO98/57606

PCT Pub. Date: Dec. 23, 1998

(30) Foreign Application Priority Data

Jun. 18, 1997 (CH) .................................................. 1487/97
Jun. 18, 1997 (CH) .................................................. 1488/97

(51) Int. Cl.$^7$ .................................................. G02B 27/00
(52) U.S. Cl. .................. 359/601; 359/603; 359/604; 359/608; 359/609; 359/610
(58) Field of Search .................. 359/601, 603, 359/604, 608, 609, 610

(56) References Cited

U.S. PATENT DOCUMENTS

| | | | |
|---|---|---|---|
| 4,130,903 | 12/1978 | van den Berg et al. | 2/8 |
| 4,155,122 | * 5/1979 | Budmiger | 2/8 |
| 5,510,609 | 4/1996 | Ackermann | 250/201.1 |
| 5,930,047 | * 7/1999 | Gunz et al. | 359/601 |
| 6,096,212 | * 8/2000 | Quick et al. | 210/493.2 |

FOREIGN PATENT DOCUMENTS

| | | |
|---|---|---|
| 25 50 559 | 9/1977 | (DE) . |
| 0 642 776A1 | 3/1995 | (EP) . |
| 0 678 288A2 | 10/1996 | (EP) . |
| 2 122 366A | 1/1984 | (GB) . |
| 96/10767 | 4/1996 | (WO) . |
| 97/15255 | 5/1997 | (WO) . |

* cited by examiner

Primary Examiner—Mohammad Sikder
(74) Attorney, Agent, or Firm—Burns, Doane, Swecker & Mathis, L.L.P.

(57) ABSTRACT

An active electro-optical filtering device, such as a glare-protection device is disclosed. The device is equipped with a light-protection filter having at least one active optical filter element, an electronic device for controlling the active filter element, a light sensor working together with the electronic device, and an electrical current supply for the electronic device and the at least one active filter element. In order to improve the efficiency in production and employment, the light-protection filter is arranged in a filter component and the electronic device, the light sensor and the electric current supply are arranged in a physically separate control component, wherein the filter components can be releasably connected mechanically and electrically to form a total unit, and for this purpose, are equipped with mutually cooperating mechanical and electrical connecting elements. In order to provide the user in his work with a viewing sense which is physiologically least disruptive in all viewing directions through the filter element and to meet basic requirements in regard to safety, such as improved spatial vision and therefore an unhampered sense of balance and the detection of approaching objects, the light-protection filter is provided with at least one optically active or passive compensation element such as an optical phase delay foil or an electro-optical filter for improving homogeneity of the light transmission, which is a function of the viewing angle. In addition, the light-protection filter is equipped with a field of vision adapted to the natural visual perception.

23 Claims, 5 Drawing Sheets

ACTIVE ELECTRO-OPTICAL FILTER DEVICE AND GLARE-PROTECTION DEVICE

FIELD OF THE INVENTION

The invention relates to an electro-optical filtering device and more particularly, to a glare-protection device.

BACKGROUND OF THE INVENTION

A filter device is used as a glare-protection device, for example, in protective welders' masks, welders' helmets or welders' goggles. Such a device comprises a light-protection filter with at least one active optical filter element, an electronic device for controlling the at least one active optical filter element, a light sensor working together with the electronic device, an electric power supply, in particular a solar cell, for the electronic device and the at least one active filter element.

Glare-protection devices of this type are known, for example from WO 96/10767 and EP-A-0 678 288. Usually they contain a liquid crystal cell (LC cell) as the active filter element, which more or less blocks the penetration of light as soon as the light sensor is acted upon by light past a preset intensity threshold. Such filter devices have many uses, a typical example is the use as windows for protective welders' masks, welders' helmets or welders' goggles.

The filter devices described in the mentioned publications are designed as so-called "monoblocs", i.e. they physically consist of a single component containing all functional elements of the filter device. Here, the functional elements have been encapsulated in a thin plate and in this way are protected from the effects of the surroundings. Because of the design as a thin, plate-shaped monobloc, the physical compatibility with the common passive light-protection filters (dark glasses) is achieved, so that the filter device can be directly exchanged against such passive light-protection filters. By means of this it is possible to retrofit glare-protection devices equipped with passive light-protection filters in a simple way by means of the more effective and more advantageous active electro-optical filter devices.

However, designing the filter in the form of a monobloc has the important economical disadvantage, also doubtful for reasons of protecting the environment, that the filter device as a whole must always be replaced, even if only one of its functional elements fails. Because of the encapsulated structure, a repair of the functional elements is as good as impossible.

SUMMARY OF THE INVENTION

This disadvantage is now intended to be overcome by a first aspect of the present invention, and the efficiency and multiplicity of use of an active electro-optical filter device of the type in accordance with the species is to be improved.

With an exemplary embodiment in accordance therewith, the filter component and the control component are embodied as physically separate components, which can be mechanically and electrically separated from each other, or respectively combined with each other to form a single unit, and to this end they are provided with mutually cooperating mechanical and electric components.

The filter component containing the light-protection filter, and the control component containing the electronics, the light sensor and the electrical power supply, are each preferably designed as encapsulated plates having a constant thickness of 1 to 5 mm for example. The filter component and the control component can also be of different thickness.

In accordance with this first basic concept of the invention, the filter device is therefore divided into two (or several) separate components, which are releasably connected with each other. Because of this division, in case of the loss of a functional element it is necessary to only replace the respective component. Furthermore, the division in accordance with the invention into control and filter components permits an increased constructive flexibility since, for example, the same control component can be employed together with different filter components. This results in considerable practical and economic advantages, both in use as well as in production.

The conventional filter devices described in the publications mentioned at the outset consist of active and passive filter elements with optical polarizers, which offer sufficient protection against ultraviolet, visible and infrared radiation and whose embodiment in the normal case includes a window designed in accordance with current production standards, such as EN 379 (90×35 mm) and EN 166 (96×25 mm). These windows are usually not sufficiently matched in the homogeneity of their light distribution to the right and the left eye to human visual perceptions, in particular if they use certain optically anisotropic technologies, or if they have been installed in an awkward position in a glare-protection cassette and protective welding mask. Besides a protection against optical radiation, protective devices should provide physiologically unhampered vision. Physiologically unhampered vision makes spatial vision easier, therefore assuring a sufficient feeling of balance, and provides protection from approaching objects. Interfering situations in the immediate area can be better detected by the user and therefore make his own actions easier.

When used as glare-protection devices, electro-optical filtering devices must be designed in such a way that the filtering devices interfere as little as possible with the effects of chronological and local actions on the eyes. This can only be assured if the geometric dimensions of the filter and its physical properties only affect and limit the information in a defined manner.

It is important for interference-free stereoscopic vision, or respectively the perception of spatial depth, and therefore for the orientation in space, that both eyes perceive the same brightness of the same object, along with a sufficient size of the field of vision. In this case the entire field of vision must not be homogeneously weakened by the same amount. It is only necessary to offer the same strength of illumination of the same object in the same viewing direction of the left and right eye.

A further important aspect of the present invention is to overcome these difficulties and to improve a glare-protection device of the type of the species designed as a mask, helmet or goggles in such a way that, in its employment in his work, it provides the user with a visual perception with the least physiological interference in all viewing directions possible through the filtering element, which therefore better meets basic requirements relating to safety, as well as improved spatial vision and therefore also an undisturbed feeling of balance and recognition of approaching objects.

In accordance with a further aspect of the invention, the dependence on the viewing angle of the light transmitted by the active optical filtering element is compensated by means of optically active or passive phase retardation elements (so-called retarders) in order to obtain a more homogeneous intensity distribution with less dependence on the viewing angle. The glare-protection device is equipped with a field of vision which is matched to the natural visual perception.

With the glare-protection device in accordance with the invention, the combination of these two measures, i.e. the homogenization of the light distribution to both eyes with every shape and size of the filtering device by means of the employment of active and/or passive optical retarders, and the increase of the lateral field of vision of the filtering device, contributes to meeting the requirement for improved visual perception under extreme light conditions, for example in connection with electric welding.

BRIEF DESCRIPTION OF THE DRAWINGS

The invention will be explained in greater detail in what follows by means of the drawings. Shown are in.

DETAILED DESCRIPTION OF THE INVENTION

Figure 1:
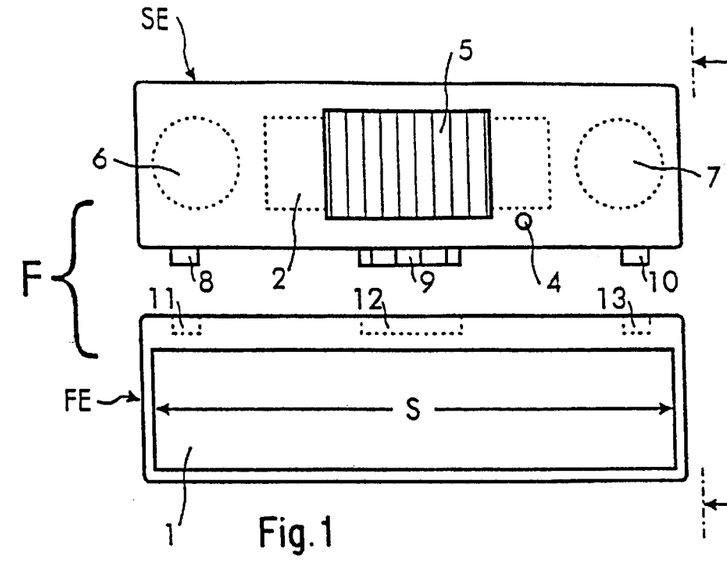
FIG. 1, a first exemplary embodiment of the filtering device in accordance with the invention with separate control and filter components, FIG. 2, a lateral view along the line II—II in FIG. 1, FIG. 3, a second exemplary embodiment with two filter components, FIG. 4, a further exemplary embodiment, FIG. 5, the filtering device in FIG. 1 in the assembled state, FIG. 6, a further exemplary embodiment similar to FIG. 3, but with filter components arranged inclined in relation to the control component, FIG. 7, a cylindrically curved filter component, FIG. 8, a spherically curved filter component, FIG. 9, a sketch for explaining the interior structure of a light-protection filter contained in the filter component(s), FIGS. 10 and 11, two isocontrast diagrams for explaining the function of the compensating elements contained in the light-protection filter, and FIGS. 12 and 13, two sketches for explaining the geometric relationships and the sizes of the fields of vision of the light-protection filter, or respectively the glare-protection device.
Figure 2:
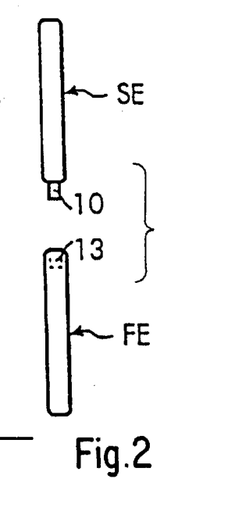

The electro-optical filtering device, identified as a whole by F in FIG. 1, is shown in the representation as having two separate components, namely a control component SE and a filter component FE, each of which is embodied in the form of a thin plate of a thickness of approximately 1 to 5 mm. The two components are preferably, but not necessarily, encapsulated. The thickness of the plates of the filter component FE and the control component SE can be different.

Figure 9:
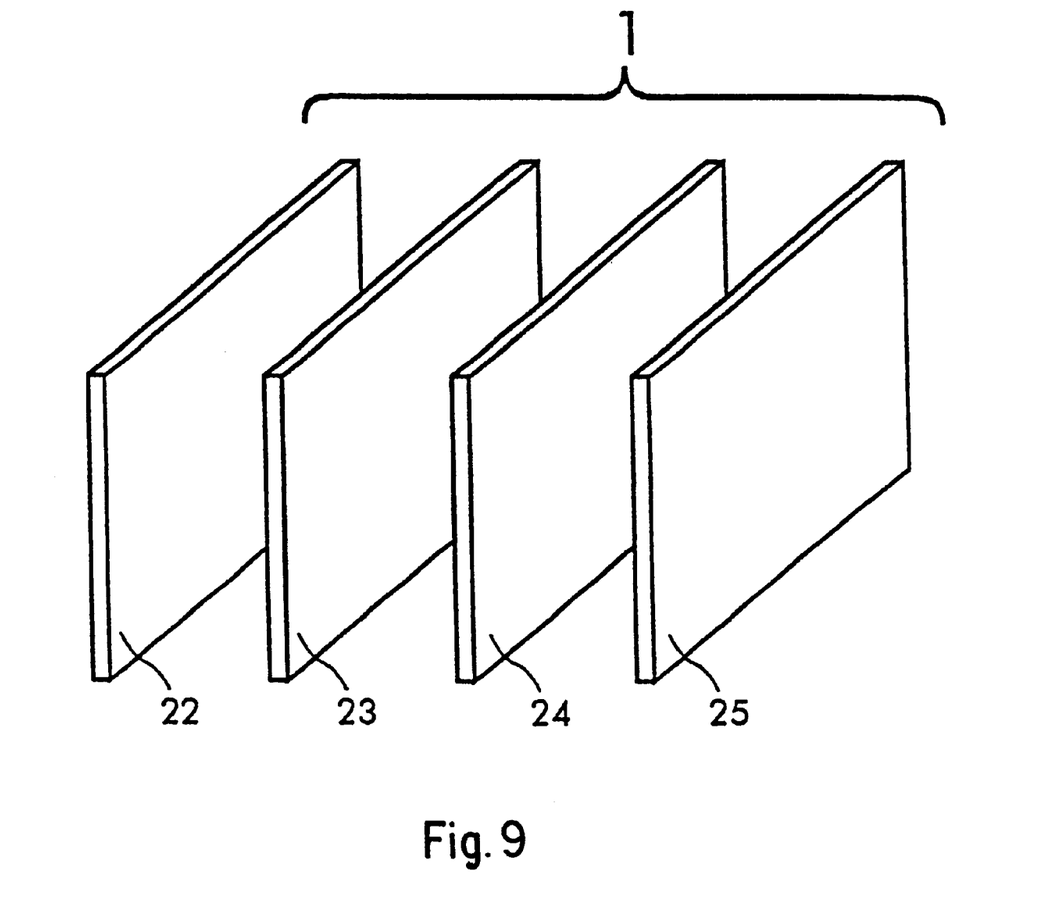

A light-protection filter 1 is provided in the filter component FE, which essentially comprises an active optical filter element 23 and its associated passive filter elements, such as UV and IR filters and polarization filters 22 and 24 placed in front and behind thereof, in particular (FIG. 9). The active filter element 23 is preferably designed as a liquid crystal cell (LC cell). Furthermore, in accordance with the invention the light-protection filter 1 contains at least one optically active or passive compensating element 25 for improving the homogeneity of the light transmission, which in particular is a function of the viewing angle. The detailed structure of the light-protection filter 1 can be seen in FIG. 9, and will be explained in greater detail. The light-protective filter 1 can of course also have several active optical filter element and correspondingly several associated passive filter elements, as well as several active or passive compensating elements.

The control component SE comprises an electronic control device 2, a light sensor 4 working together with the control device, and an electric power supply which itself contains a solar cell 5 and two rechargeable battery cells 6 and 7. The electrical power supply can of course also be provided in a different way, for example with only one or several solar cells, or with only one or several battery cells.

The control component SE is provided with mechanical and electrical connecting elements 8, 9 and 10, which work together with complementary mechanical and electrical connecting elements 11, 12 and 13 on the filter component FE in such a way that the control and the filter components can be connected with each other in a mechanically and electrically releasable manner. In the exemplary embodiment represented, the connecting elements constitute a plug connection, but any other type of connection is also possible. The filtering device F is shown in the assembled state in FIG. 5.

In the exemplary embodiment represented, the battery cells 6 and 7 can be recharged by the solar cell 5 via the electronic control device 2, or they are used as a safety backup system. If light exceeding a predetermined intensity threshold impinges on the light sensor 4, the electronic control device 2 generates a control signal for the light protection filter 1, so that the filtering element becomes more or less impervious to light. Conversely, the active filter element again becomes transparent when light of sufficient intensity no longer impinges on the light sensor 4.

Aside from its division into physically separated components and from the additional details (compensating element 25, size of the field of vision) to be explained further, the structure and the function of the filtering device in accordance with the invention completely corresponds to the filtering devices described in the documents mentioned at the outset, so that one skilled in the art does not require more detailed explanations in this regard.

Among other benefits, the division into separate components permits an increased freedom of the structural design. For example, the filtering device in accordance with FIG. 3 or FIG. 6 can also be provided with two or more filter components FE, even of different sizes, each of which operates together with the same control component SE. Here, the filter components FE can also be arranged at a mutual distance from each other, such as in normal eyeglasses.

Figure 4:
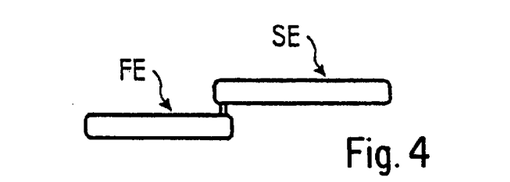
Figure 5:
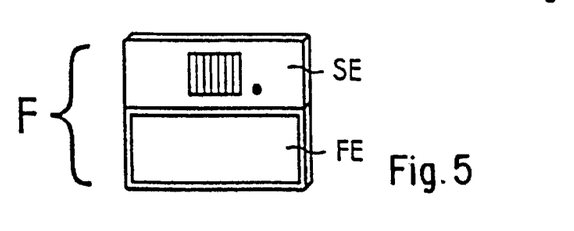
Figure 6:
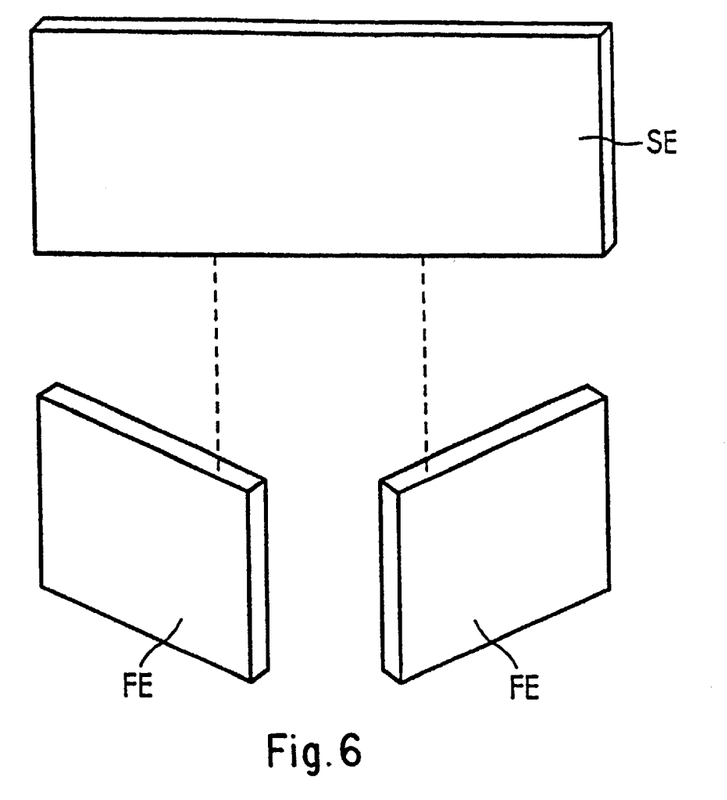

In the exemplary embodiment of FIGS. 1 and 5, the two components SE and FE are located in one plane in the assembled state and therefore result outwardly in a filtering device analogous to WO 96/10767, without having the disadvantages of the latter. But the components SE and FE can also be designed in such a way that, in the assembled state, they are located in two planes which are parallel, as represented in a simplified manner in FIG. 4. Finally, the control component SE and the filter component FE can also be put together at an angle, as represented in FIG. 6.

Figure 7:
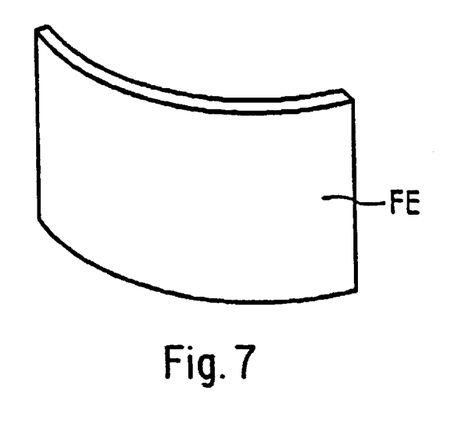
Figure 8:
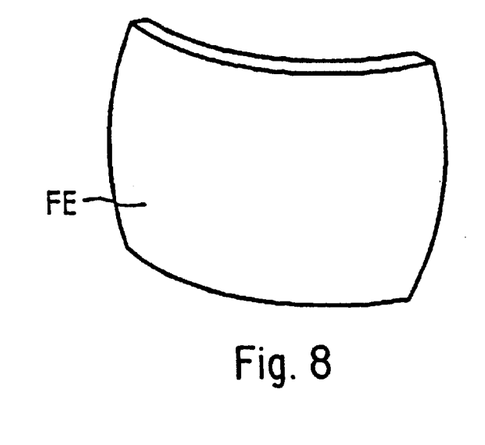

The filter components FE can be designed as flat plates (FIGS. 1 to 6) or spatially curved (FIGS. 7 and 8).

Because of dividing the filtering device into two or more components, the latter are smaller and can be produced with little constructive effort, so they are inherently rigid and self-supporting. Moreover, they can be made thinner and therefore also lighter. It is also possible to match their dimensions more easily and more simply to existing conditions. For example, in the case of a glare-protecting mask, the filter components can be brought closer to the eye.

It is understood that the control component SE can also be conceived in such a way that it is intended to essentially remain fixed in place within a glare-protecting device, for example a welders' mask. In this case only the filter component FE can be easily replaced.

As already mentioned, an important aspect of the present invention lies in the compensating measures for the transmission properties which are a function of the viewing angle and the inhomogeneous intensity distribution of the at least one active filter element 23 designed as an LCD connected with this. This compensation is provided with the aid of an optically active or passive compensating element which affects the phase behavior of the electromagnetic field vector in every spatial direction in such a way that a homogenization of the local and angle-dependent radiation distribution is achieved by means of the light-protection filter. Active or passive phase delay elements (so called optical retarders) are suitable as compensating elements. Passive phase compensation foils (retarder foils, "phase-matched biaxial compensation film") are particularly preferred. The structure and functioning of such compensating elements, in particular retarder foils, are known to one skilled in the art and have been described, for example, in an article by S. T. Wu in the SID 95 DIGEST on pages 555 to 558.

Figure 10:
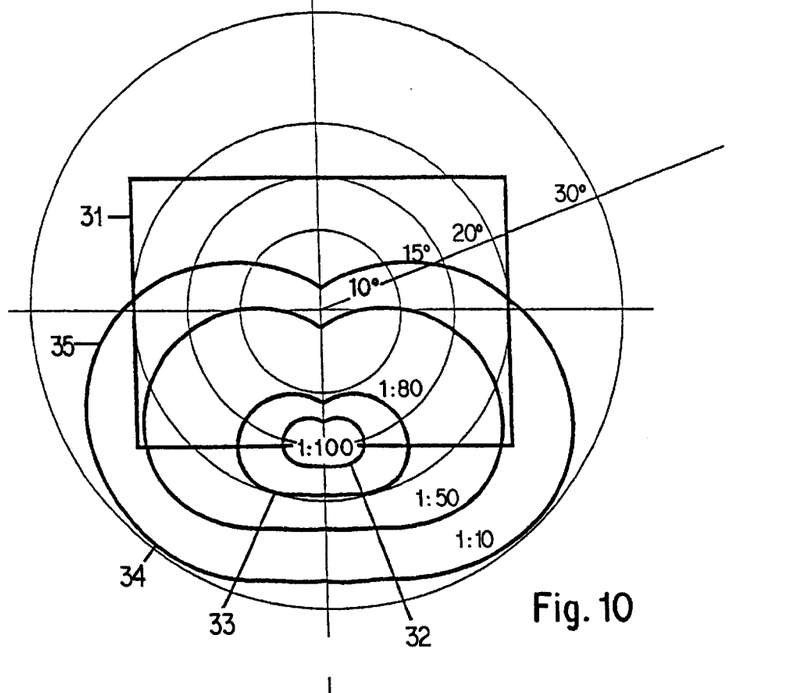

FIG. 10 shows the transmission properties of a conventional light-protection filter without the compensation in accordance with the invention in the form of an isocontrast diagram. Contrast here is understood to be the ratio of the transmitted light intensities in the impervious and in the pervious state of the light-protection filter. The rectangular field 31 defines a minimal field of vision in which, in accordance with the standard, a minimal amount of stereoscopic sight is just barely possible. The curves 32 to 35 respectively connect the locations of equal contrast, namely from the inside to the outside for 1:100, 1:80, 1:50 and 1:10. As can be seen, the degree of transmission is a function of the viewing angle and is extremely inhomogeneous over the field of vision.

Figure 11:
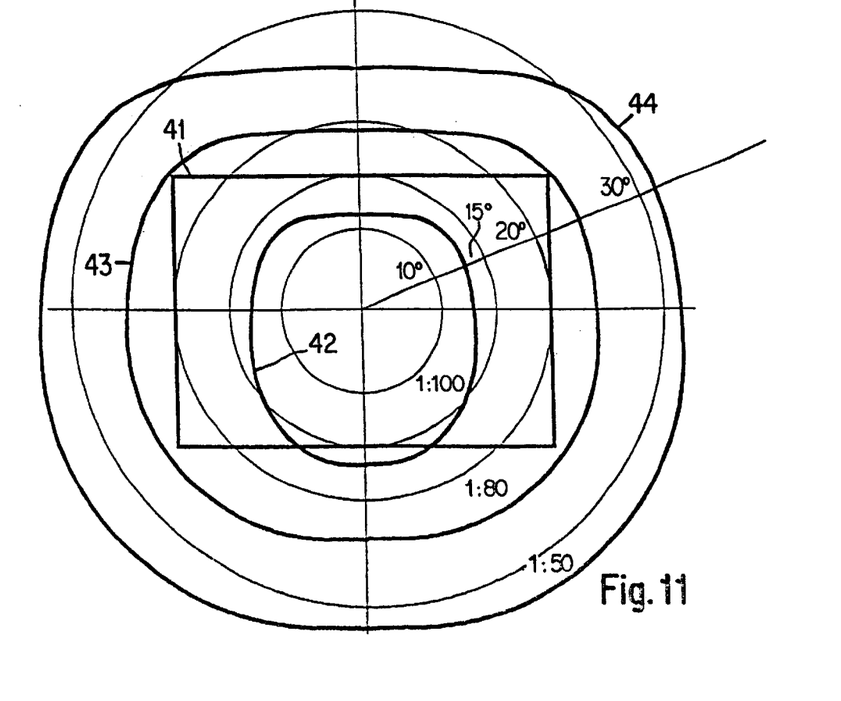

FIG. 11 shows an analogous isocontrast diagram for a light-protection filter equipped in accordance with the invention with a compensating element. The minimal field of vision is marked by a rectangle 41, the curves 42 to 44 again respectively connect the locations of equal contrast, namely from the inside to the outside for 1:100, 1:80 and 1:50. As can be seen, the degrees of transmission are now considerably more homogeneous and in particular do not fall below 1:80 over the entire field of vision 41. It is therefore easily possible with this configuration to considerably increase the field of vision.

The adaptation of the field of vision which, inter alia, is defined by the dimensions of the light-protection filter, to the natural visual perception is a further essential aspect of the present invention. Essentially the lateral field of vision is addressed here.

As already mentioned at the outset, a minimum size of the field of vision of 96 mm×25 mm (EN 166), or respectively 90 mm×35 mm (EN 379) is required by the EN/DIN production standard in order to assure a minimum of stereoscopic vision. This approximately corresponds to a viewing angle range of ±20° horizontally and ±15° vertically.

The geometrical conditions for the practical use of the filtering device, for example as a glare-protection device, can be described by the following approximation equation:

$$S \cong D - \frac{2*D*d}{r+d} + k*d$$

wherein:
D=average eye distance [mm]
d=distance eye to light-protection filter [mm]
r=distance light-protective filter to work point [mm]
S=lateral (horizontal) size of field of vision [mm]
k="field of vision constant" (dimensionless)

Figure 3:
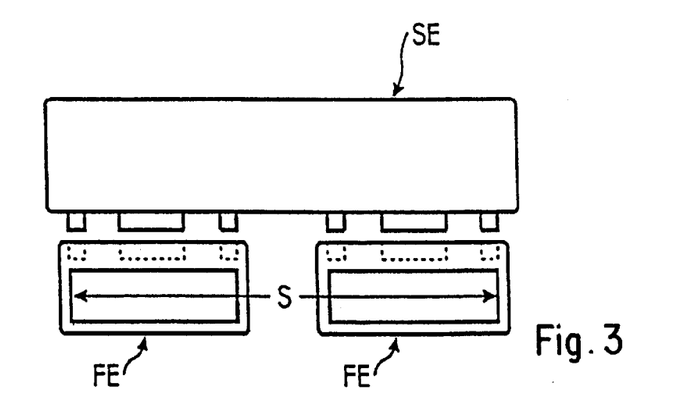
Figure 12:
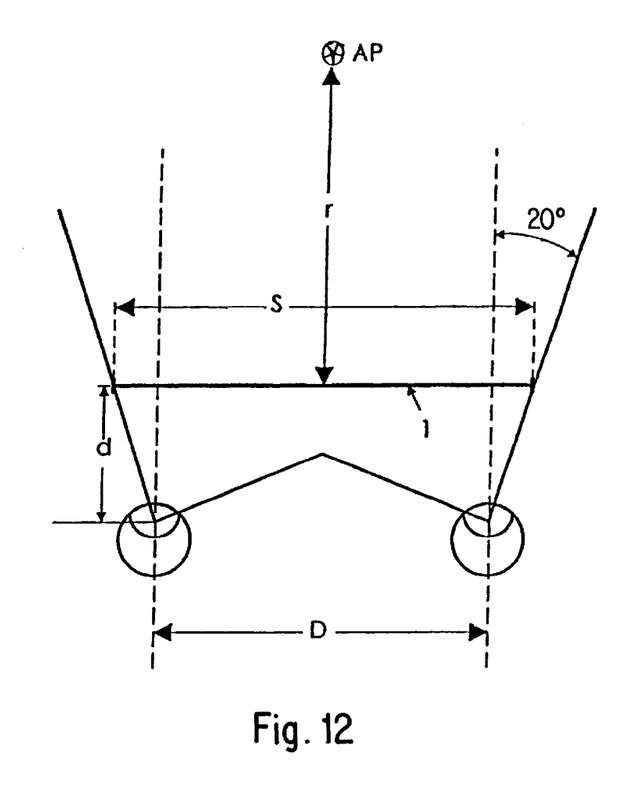
Figure 13:
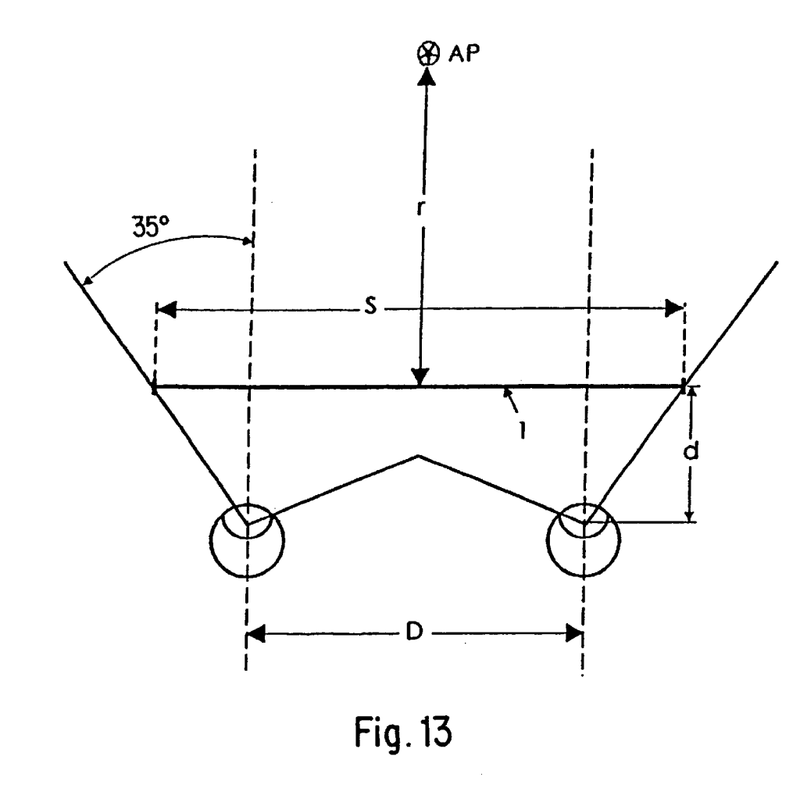

FIGS. 12 and 13 make this clear. The work point AP is understood to be the point on which the sight is concentrated when working, i.e. in the case of welding work, the location of the welding arc. The average eye distance D and the distance r to the working point are standard values (64 mm, or respectively 400 mm) in actuality, so that the approximation equation essentially represents the connection between the distance d of the light-protection filter from the eye, the lateral size of the field of vision S and the field of vision constant k. With customary glare-protection masks at least, the distance d is approximately 60 mm. In the case of two separate filter components FE, the lateral size of the field of vision is understood to be the lateral outer measurement of the configuration composed of the two light-protection filters (FIG. 3).

Based on the above standard sizes for the field of vision and with r=400 mm and a greatest distance d of 60 mm, a field of vision constant k=0.85 is calculated as a minimum value for stereoscopic vision. In other words: under the usual practical conditions, a lateral size of the field of vision which allows the minimum amount of stereoscopic vision in accordance with the standard, results with a field of vision constant k=0.85 (FIG. 12).

In accordance with a further essential aspect of the invention, the geometrical conditions of the filtering device are now changed in such a way that they meet the above mentioned relationship wherein, however, the value for the field of vision constant is at least 1.15. Preferably k has a value greater than 2, in particular 2.22. With the last mentioned value of the field of vision constant k a lateral size of the field of vision results, which assures optimum stereoscopic vision and therefore an optimum spatial orientation capability. FIG. 13 makes the relationships clear, for example for a value of the field of vision constant of k=1.38.

The dimensioning in accordance with the invention of the filtering device essentially aims for a relative enlargement of the lateral field of vision. However, the desired result only occurs if the degree of transmission of the light-protection filters over this increased field of vision is sufficiently homogeneous. As explained above, the latter is assured by the compensating steps in accordance with the invention.

Often, commercially available electro-optical filtering devices do not meet these requirements for an increased lateral field of vision because of the glare-protection device based on the liquid crystal technology employed, or as a result of structural deficiencies, and at most are limited to meeting customary standards. The present invention makes possible the realization of a viewing angle range of the glare-protection device, which is optimally matched to the human sense of viewing in relation to safety, by the combined employment of suitable, geometrically constructive and optically phase-correcting steps which are employed in addition to the light-protection filter.

Optically active and passive delay measures make possible a specific influence of the angle-dependent transmission properties of the electro-optical filter for improving the binocular vision effect, the maximally possible resolution and the spatial perception by the vision apparatus.

The last described two main aspects of the invention increase the safety of the protective device by the employment of optically active and passive retarders independently of the size of the field of vision for compensating the angle-dependent transmission of any arbitrary electro-optical filter, and secondly by a geometrical adaptation of the electro-optical light-protection filter to the physiological viewing requirements of the observer.

Because of the division of the filtering device in accordance with the first described main aspect of the invention into two or more separate, releasably connected components, the latter are smaller and can be produced with little constructive outlay to be inherently rigid and self-supporting. Moreover, they can be embodied to be thinner and correspondingly lighter. It is furthermore possible to match their dimensions more easily and simpler to existing conditions. For example, in the case of a glare-protecting mask the filter components can be brought closer to the eye. Furthermore, in case of the outage of a function element it is only necessary to replace the respective component.

The combination of the three main aspects of the invention mentioned results in a filtering device which is optimal both in relation to production technology as well as in practical use.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. An electro-optical filtering device comprising:
    a light-protection filter with at least one active optical filter element;
    an electronic device for controlling the at least one active filter element;
    a light sensor working together with the electronic device; and
    an electrical current supply for the electronic device and the at least one active filter element, wherein the light-protection filter is arranged in a filter component and the electronic device, the light sensor and the electric current supply are arranged in a control component, the filter component and the control component being embodied as physically seperate components equipped with mutually cooperating mechanical and electrical connecting elements such that the filter component and the control component can be mechanically and electrically separated from each other, and are releasingly combined with each other via said connecting elements to form the electro-optical filtering device.

2. The filtering device in accordance with claim 1, wherein the filter component is embodied as at least one of a flat and curved plate having a thickness of between 1 and 5 mm.

3. The filtering device in accordance with claim 1, wherein the control component is embodied as a plate of a thickness of between 1 and 5 mm.

4. The filtering device in accordance with claim 1, wherein the filter component and the control component are encapsulated.

5. An electro-optical filtering device comprising:
    a light-protection filter with at least one active optical filter element;
    an electronic device for controlling the at least one active filter element;
    a light sensor working together with the electronic device; and
    an electrical current supply for the electronic device and the at least one active filter element, wherein the light-protection filter is arranged in a filter component and the electronic device, the light sensor and the electric current supply are arranged in a control component, the filter component and the control component being embodied as physically separate components equipped with mutually cooperating mechanical and electrical connecting elements such that the filter component and the control component can be mechanically and electrically separated from each other, and wherein at least two filter components are provided, which can be releasably mechanically and electrically connected with the control component.

6. The filtering device in accordance with claim 1, in the state wherein the components are combined into a total unit, the control component and the filter component are arranged in one plane or in planes which are parallel in relation to each other.

7. The filtering device in accordance with claim 1, wherein the filter component is embodied to be at least one of cylindrically curved and spherically curved.

8. An electro-optical filtering device comprising:
    a light-protection filter with at least one active optical filter element, wherein the light-protection filter is provided with at least one optical compensating element which affects a phase behavior of an electromagnetic field vector in every spatial direction in such a way, that a homogenization of a local and angle-dependent radiation distribution by the light-protection filter is achieved;
    an electronic device for controlling the at least one active filter element;
    a light sensor working together with the electronic device; and
    an electrical current supply for the electronic device and the at least one active filter element, wherein the light-protection filter is arranged in a filter component and the electronic device, the light sensor and the electric current supply are arranged in a control component, the filter component and the control component being embodied as physically separate components equipped with mutually cooperating mechanical and electrical connecting elements such that the filter component and the control component can be mechanically and electrically separated from each other, and are releasingly combined with each other via said connecting elements to form the electro-optical filtering device.

9. The filtering device in accordance with claim 8, wherein the compensating element is embodied as an optical phase compensation foil.

10. A glare-protection device for welding work, said device comprising an active electro-optical filter device located at a distance in front of eyes of a person wearing the glare-protection device, wherein the filtering device further comprises:
    a light-protection filter with at least one active optical filter element;
    an electronic device for controlling the at least one active filter element;

a light sensor working together with the electronic device; and an electrical current supply for the electronic device and the at least one active filter element, wherein the light-protection filter is provided with at least one optical compensating element which affects a phase behavior of an electromagnetic field vector in every spatial direction in such a way that a homogenization of a local and angle-dependent radiation distribution by the light-protection filter is achieved and the light-protection sensor has a lateral field of vision size (S) which satisfies the equation $$S \cong D - \frac{2*D*d}{400+d} + k*d$$

wherein D is an average eye distance of a person wearing the glare-protection device, d is a distance of the light-protection filter from the eye, and k is a field of vision constant $\geq 1.15$.

11. A glare-protection device for welding work, said device comprising an active electro-optical filter device located at a distance in front of eyes of a person wearing the glare-protection device, wherein the filtering device further comprises:

a light-protection filter with at least one active optical filter element;

an electronic device for controlling the at least one active filter element;

a light sensor working together with the electronic device; and an electrical current supply for the electronic device and the at least one active filter element, wherein the light-protection filter is provided with at least one optical compensating element which affects a phase behavior of an electromagnetic field vector in every spatial direction in such a way that a homogenization of a local and angle-dependent radiation distribution by the light-protection filter is achieved and the light-protection sensor has a lateral field of vision size (S) which satisfies the equation:

$$S=47.3+60* k,$$

wherein k is a field of vision constant $\geq 1.15$.

12. The glare-protection device in accordance with claim 10, wherein the field of vision constant $k \geq 1.8$.

13. The glare-protection device in accordance with claim 10, wherein the field of vision constant $k \geq 2.2$.

14. The device of claim 1, wherein the device is a glare-protection device utilized in at least one of a welder's mask, a welders helmet and a welder's goggle.

15. The filtering device of claim 1, wherein the electrical current supply is a solar cell.

16. The filtering device of claim 10, wherein said device is one of a mask, a helmet and goggles.

17. The device of claim 10, wherein the electrical current supply is a solar cell.

18. The device of claim 10, wherein the at least one optical compensating element is an optical phase compensation foil.

19. The device of claim 11, wherein said device is one of a mask, a helmet and goggles.

20. The device of claim 11, wherein the electrical current supply is a solar cell.

21. The device of claim 11, wherein the at least one optical compensating element is an optical phase compensation foil.

22. The glare-protection device in accordance with claim 11 wherein the field of vision constant $k \geq 1.8$.

23. The glare-protection device in accordance with claim 11 wherein the field of vision constant $k \geq 2.2$.

* * * * *